United States Patent [19]

Evans et al.

[11] Patent Number: 5,714,351

[45] Date of Patent: Feb. 3, 1998

[54] CYCLOPENTENES

[75] Inventors: Christopher Thomas Evans, Hertfordshire; Stanley Michael Roberts, Devon; Karoline Shoberu, Chelmsford; Rosemary Mackeith, Exeter, all of England

[73] Assignee: Chiroscience Limited, Cambridge, England

[21] Appl. No.: 211,623

[22] PCT Filed: Apr. 21, 1992

[86] PCT No.: PCT/GB92/00730

§ 371 Date: Feb. 13, 1995

§ 102(e) Date: Feb. 13, 1995

[87] PCT Pub. No.: WO92/18444

PCT Pub. Date: Oct. 29, 1992

[30] Foreign Application Priority Data

Apr. 19, 1991 [GB] United Kingdom ............... 9108376

[51] Int. Cl.$^6$ .............. C12P 19/38; C12P 19/40; C12P 9/00; C12P 7/02
[52] U.S. Cl. .............. 435/87; 435/88; 435/131; 435/132; 435/135; 435/155; 435/196; 435/197; 435/280; 435/876; 556/437; 556/449; 560/201; 560/205; 568/763; 568/838
[58] Field of Search ................ 435/132, 155, 435/135, 196, 197, 876, 87, 88, 280, 131; 549/311; 568/838, 763; 560/205, 201; 556/437, 449

[56] References Cited

U.S. PATENT DOCUMENTS

| | | | |
|---|---|---|---|
| 3,965,118 | 6/1976 | Van Rheenen | 549/311 |
| 4,170,596 | 10/1979 | Yamada et al. | 560/12 |
| 4,217,284 | 8/1980 | Yamada et al. | 549/311 |
| 4,618,690 | 10/1986 | Schneider et al. | 556/441 |
| 4,916,224 | 4/1990 | Vince et al. | 544/254 |
| 4,950,758 | 8/1990 | Vince et al. | 544/276 |
| 4,963,492 | 10/1990 | Keller et al. | 435/280 |
| 5,057,630 | 10/1991 | Lackey et al. | 568/838 |

FOREIGN PATENT DOCUMENTS

| | | |
|---|---|---|
| 0 115 860 | 8/1984 | European Pat. Off. . |
| 0 127 386 | 12/1984 | European Pat. Off. . |
| 0 149 674 | 7/1985 | European Pat. Off. . |
| 0 212 956 | 3/1987 | European Pat. Off. . |
| 0 267 878 | 5/1988 | European Pat. Off. . |
| 0 271 433 | 6/1988 | European Pat. Off. . |
| 0 419 988 | 4/1991 | European Pat. Off. . |
| 0 434 450 | 6/1991 | European Pat. Off. . |
| 0 501 310 | 9/1992 | European Pat. Off. . |
| 37 24 721 | 4/1989 | Germany . |
| WO 92/18444 | 10/1992 | WIPO . |

OTHER PUBLICATIONS

E. Saville–Stones, et al., "Synthesis of (±)-2',3'-Didehydro-2',3'-dideoxy Nucleosides via a Modified Prins Reaction and Palladium (O) Catalysed Coupling", J. Chem. Soc. Perkin Trans. 1, No. 10, Oct. 1991, pp. 2603–2604.

C. Evans, et al., "Potential Use of Carbocyclic Nucleosides for the Treatment of AIDS: Chemo–enzymatic Syntheses of the Enantiomers of Carbovir", J. Chem. Soc. Perkin Transc. 1, No. 5, Oct. 1991, pp. 589–592.

S. Roberts, et al., "Enzymatic Resolution of cis– and trans–4–Hydroxycyclopent–2–enylmethanol Derivatives and a Novel Preparation of Carbocyclic 2',3'–Dideoxydi–dehydronucleosides and Aristeromycin", J. Chem. Soc. Perkin Trans. 1, No. 10, Oct. 1991, pp. 2605–2607.

Grieco et al., "Total Synthesis of (±)–Sesbanimide A and B", Journal Of The Chemical Society, Chemical Communications, No. 4, pp. 369–370, published Feb. 15, 1992.

Lubineau et al., "Hetero Diels–Alder Reaction In Water. Synthesis Of α–Hydroxy–γ–Lactones", Tetrahedron Letters, vol. 32, No. 51, pp. 7529–7530, published Dec. 16, 1991.

Sustmann et al., "Thermolyse von Perestern mit Bicyclo [3.1.0]hexangeruest", Chemische Berichte, vol. 109, pp. 444–454, published 1976.

Morrison & Boyd "Organic Chemistry" 3rd Ed. Publishers Allyn & Bacon Inc. Boston 1973 p. 284.

CRC "Handbook of Chemistry & Physics" 51st Ed 1970–1971 Ed. Weast p. C–8.

*Primary Examiner*—Herbert J. Lilling
*Attorney, Agent, or Firm*—Foley & Lardner

[57] ABSTRACT

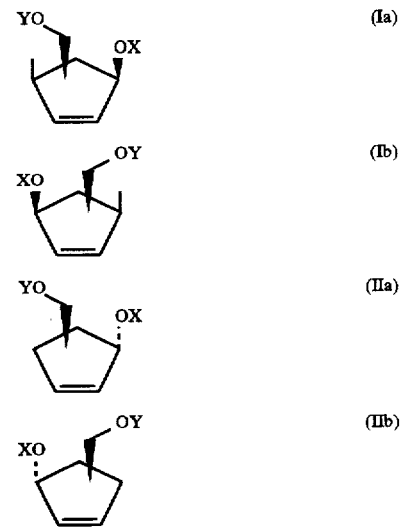

The individual enantiomers of the compounds (Ia), (Ib), (IIa) or (IIb), optionally substituted by non-interfering substituent(s). The novel enantiomers can be obtained by biotransformation. The (Ia) or (IIa) compounds can be used for the synthesis of chiral carbocyclic nucleosides.

17 Claims, No Drawings

CYCLOPENTENES

FIELD OF THE INVENTION

This invention relates to cyclopentene derivatives and also to their preparation and use.

BACKGROUND OF THE INVENTION

Carbocyclic nucleosides such as Carbovir are of therapeutic value. Their stereospecific synthesis is important.

EP-A-0424064 describes the enantioselective hydrolysis of the γ-lactam 2-azabicyclo[2.2.1]hept-5-en-3-one, utilising enzymatic activity available in deposits NCIMB 40213 and 40249. See also Taylor et al, J. Chem. Soc. Chem. Comm. (1990) 1120.

SUMMARY OF THE INVENTION

This application concerns the enantiomers of cyclopentene derivatives of structures Ia, Ib, IIa and IIb wherein X (at the 1-position) represents hydrogen or an acyl group, and Y (on the $CH_2OY$ group which is at the 4 or 5-position) represents hydrogen or a group that can be readily replaced by hydrogen, i.e. a protecting group, such as an acyl, triarylmethyl or trialkylsilyl group. These novel compounds may each be provided substantially free of other enantiomers.

DESCRIPTION OF THE INVENTION

An aspect of the invention is the means to introduce a heterocyclic base such as adenine in a single step to form a protected or unprotected carbocyclic nucleoside of formula III. Thus, for example, treatment of cyclopentene Ia (X=Ac, Y=H) with adenine in the presence of, say, a catalyst such as tetrakis(triphenylphosphine)palladium(O) and sodium hydride gives an unprotected nucleoside (III); similarly, treatment of cyclopentene Ia (X=Ac, Y=CPh$_3$) with 6-chloropurine gives a protected nucleoside (III). Alternatively, direct reaction of IIa (X=H, Y=CPh$_3$) with chloropurine in the presence of triphenylphosphine and diethyl azodicarboxylate (Mitsunobu conditions) also gives III. Similarly, Ib and IIb give an enantiomer of III.

The key individual enantiomeric synthons of this invention, Ia, Ib, IIa and IIb may be prepared from racemic mixtures Ia+Ib and IIa+IIb, wherein X=Ac or H by either lipase-catalysed enantioselective deacylation (X=Ac→X=H) or lipase-catalysed enantioselective acylation with vinyl acetate (X=H→X=Ac). A suitable lipase for the purpose is *Pseudomonas fluorescens* lipase, in which case the enantiomers Ib and IIb are substrates for the enzyme and Ia and IIa are not. The absolute configurations of the products may be determined by correlation with the tetraol of formula IV for which the assignment is known (see Tadano et al, J. Org. Chem. 54 (1989) 276), after dihydroxylation with osmium tetroxide.

The racemic compounds used as substrates for the biocatalytic resolution may be made by known methods. For example, the compounds in which $CH_2OY$ is at the 4-position may be prepared by the Prins reaction onto cyclopentadiene. Such methods are described by Bajorek et al, J. Chem. Soc. Perkin Trans. 1 (1947) 1243, and Pawson et al, Chem. Ber. 114 (1981) 346. The reaction affords a mixture of diastereoisomers Ia/Ib+IIa/IIb, wherein X=Y=H. The diastereoisomers are separated conveniently as the trityl derivative (X=H, Y=CPh$_3$), for instance by chromatography on silica gel. The group Y may be left as trityl in the biotransformation or altered to a different suitable protecting group such as tert-butyldimethylsilyl.

Compounds of formula I in which the $CH_2OY$ group is at the 5-position may be prepared from the cycloadduct of formula V that is obtained by reaction between cyclopentene and glyoxylic acid. The Chart (below) shows an illustrative synthetic sequence to a compound of formula III: Step 1 involves, e.g. reduction with LiAlH$_4$, treatment with NaIO$_4$ and then NaBH$_4$, and selective protection, e.g. with Ph$_3$CCl or t-BuMe$_2$SiCl; Step 2 comprises biotransformation, e.g. using a lipase, and vinyl acetate; Steo 3 comprises treatment with Pd(PPh$_3$)$_4$, adenine and NaH.

The key biotransformation step is carried out by treatment of the secondary alcohol with an acyl donor such as vinyl acetate or butyric anhydride in an organic solvent such as tetrahydrofuran. Alternatively, the racemic secondary alcohol is acylated chemically and the racemic acyl derivative subjected to biotransformation under hydrolytic conditions: either a lipase in a two-phase system of aqueous buffer and organic solvent such as toluene or by a microbial biocatalyst in an aqueous suspension of the acyl derivative.

The palladium complex-catalysed coupling reaction that enables direct incorporation of the heterocyclic base unit (possibly in protected form) proceeds via an η$^3$ π-allyl palladium complex that is common with that obtained from the isomeric cyclopentene derivatives of formula I.

The compounds of the invention may be substituted, if desired, by non-interfering substituents, i.e. substituents that do not affect the biotransformation. Examples of substituents (if present) are methyl, ethyl, n-butyl, OH, Cl, Br, F, CF$_3$ and N$_3$. The total number of C atoms in the substituent (s) will not usually exceed 8 or, more usually, 4.

The following Examples illustrate the invention specifically for the cyclopentenes having a 4-($CH_2OY$) group.

EXAMPLE 1

Ia (X=Ac, Y=SiMe$_2$tBu) [(−)-1(R)-acetoxy-4(S)-(tert-butyldimethylsilyloxymethyl)-cyclopent-2-ene] and Ib (X=H, Y=SiMe$_2$Bu) [(+)-4(R)-tert-butyldimethylsilyloxymethyl)cyclopent-2-en-1(S)-ol]

To a solution of (±)-I (X=Ac, Y=−SiMe$_2$Bu; 203.5 mg, 0.75 mmol) in acetone (2.5 ml), pH 7 phosphate buffer (12.5 ml) was added with stirring. To this, *Pseudomonas fluorescens* lipase (PFL) (96.2 mg) was added and the mixture stirred for 15 h when another aliquot of fresh enzyme was added. After a further 5 h of stirring TLC indicated approx. 50% hydrolysis. The enzyme was removed by filtration and the filtrate extracted with ether (4×40 ml). The combined organic phases were dried (MgSO$_4$), filtered, and the filtrate concentrated in vacuo. The residue (180 mg) was chromatographed on silica (9:1 petrol:ethyl acetate) to give first Ia (X=Ac, Y=SiMe$_2$tBu) (88 mg, 43%) followed by Ib (X=H, Y=SiMe$_2$tBu) (72 mg, 42%), both as oils.

Data:

Ia: $[\alpha]^{25}_D$ −4.2° (c=1.78, CHCl$_3$) (>95% ee) γmax (neat) 2934, 2860, 1736 (C=O str), 1242, 1082 cm$^{-1}$ δH (CDCl$_3$) 0.03 (S, 6H, SiMe$_2$), 0.87 (S, 9H, $^+$Bu), 1.50 (ddd, 1H, H-6) 2.00 (S, 3H, Ac), 2.40 (ddd, 1H, H-6), 2.79 (M, 1H, H-4), 3.53 (d, 2H, CH$_2$OSi), 5.61 (M, 1H, H-1), 5.82 (ddd, 1H, H-3), 6.03 (ddd, 1H, H-2).

Ib: $[\alpha]^{25}_D$ +49.6° (c=1.42, CHCl$_3$) (>95% ee) γmax (neat) 3394 (OH str), 2957, 2933, 2859, 1466, 1385, 1254, 1084, 1040, 1008 cm$^{-1}$, δH (CDCl$_3$) 0.04 (S, 6H, SiMe$_2$), 0.87 (S, 9H, $^+$Bu), 1.49 (ddd, 1H, H-6), 2.26 (ddd, 1H, H-6), 2.76 (M, 2H, H-4 and OH), 3.56–3.62 (x dd CH$_2$OSi), 4.57 (M, 1H, H-1), 5.73 (dd, 1H, H-3) and 5.90 (ddd, 1H, H-2).

EXAMPLE 2

Ia (X=H, Y=Ph$_3$C) and Ib (X=Ac, Y=Ph$_3$C)

A solution of (±)-I (X=H, Y=—Ph$_3$C; 55.4 mg, 0.16 mmol) in vinyl acetate (4 ml), was stirred with PFL (22.9 mg) for 46 h. The enzyme was removed by filtration and the filtrate concentrated in vacuo. The residue (75 mg) was chromatographed on silica (6:1 petrol:ethyl acetate) to give first Ib (X=Ac, Y=Ph$_3$C) as an oil (13.6 mg, 22%) followed by Ia (X=H, Y=Ph$_3$C) as a white solid (mp 111°–112° C.) (27.7 mg, 50%).

Data:

Ib: $[\alpha]^{27}_D$+16.2° (c=0.68, CHCl$_3$) (>95% ee) γmax (neat) 3062, 3030, 2916, 2868, 1732 (C=O str), 1490, 1445, 1366, 1240, 1067, 1021 cm$^{-1}$, δH (CDCl$_3$) 1.60 (ddd, 1H, H-6), 2.00 (S, 3H, Ac), 2.51 (ddd, H-5),2.96 (M, 1H, H-4), 3.06–3.18 (m, 2H, CH$_2$OCPh$_3$), 5.67 (M, 1H, H-1), 5.89 (dd, 1H, H-3), 6.13 (ddd, 1H, H-2), 7.03–7.50 (M, 15H, CPh$_3$).

Ia: $[\alpha]^{27}_D$-52.1° (c=1.39, CHCl$_3$) (82% ee) γmax (KBr) 3382 (OH str), 3059, 2935, 1488, 1445, 1388, 1314, 1218, 1179, 1153, 1091, 1053 and 1033 cm$^{-1}$ δH (CDCl$_3$) 1.42 (ddd, 1H, H-6) 2.13 (br.d, 1H, OH), 2.37 (ddd, 1H, H-6), 2.84 (M, 1H, H-4), 3.08 (dd, 2H, CH$_2$OCPh$_3$), 3.29 (dd, 1H, OH), 4.71 (br.s, 1H, H-1), 5.97 (S, 2H, H-2 and H-3), 7.29–745 (M, 15H, CPh$_3$).

EXAMPLE 3

IIa (X=H, Y=Ph$_3$C) and IIb (X=Ac, Y=Ph$_3$C)

A solution of (±)-II (X=H, Y=—Ph$_3$C; 53.7 mg, 0.15 mmol) in vinyl acetate (3.5 ml), was stirred with PFL (32.9 mg) for 48 h until TLC indicated approx. 50% acetylation. The enzyme was removed by filtration and the filtrate concentrated in vacuo. The residue (62.4 mg) was chromatographed on silica to give first IIb (X=Ac, Y=Ph$_3$C) as an oil (31.1 mg, 52%) followed by IIa (X=H, Y=Ph$_3$C) as a white solid, mp 101°–104° (25.7 mg, 48%).

Data:

IIb: $[\alpha]^{26}_D$-87.9° (c=1.06, CHCl$_3$) (74% ee) γmax (neat) 3062, 3030 (OH str), 2914, 2867, 1733 (C=O str), 1491, 1446, 1367, 1241, 1184, 1069 and 1022 cm$^{-1}$, δH (CDCl$_3$) 2.08 (m, 5H, 2×H-6+CH$_3$CO), 3.04–3.16 (M, 2H, CH$_2$OCPh$_3$), 3.20–3.28 (M, 1H, H-4), 5.72–5.76 (m, 1H, H-1), 5.91–5.98 (ddd, 1H, H-3), 6.20 (ddd, 1H, H-2), 7.24–7.47 (M, 15H, CPh$_3$)

IIa: $[\alpha]^{26}_D$-85.2° (c=0.99, CHCl$_3$) (74% ee) γmax (neat) 3247 (OH str), 3060, 2912, 2885, 1488, 1445, 1382, 1319, 1215, 1181, 1154, 1112, 1075 and 1047 cm$^{-1}$ δH (CDCl$_3$) 1.63 (S, 1H, OH) 1.80–1.99 (M, H-6), 2.99 (dd, 1H, CH$_2$OCPh$_3$), 3.08 (dd, 1H, CH$_2$OCPh$_3$), 3.15–3.26 (M, 1H, H-4), 4.85–492 (M, 1H, H-1), 5.89–5.94 (M, 1H, H-3), 6.06–6.12 (M, 1H, H-2), 7.22–732 (M, 9H, Ph) and 7.47–755 (M, 6H, Ph)

EXAMPLE 4

III (base=adenine, Y=H)

A suspension of adenine (91 mg, 0.7 mmol) and sodium hydride (26.3 mg, 60% dispersion) was stirred in N,N-dimethylformamide (DMF) (1.7 ml) until deprotonation was complete (4 h at ambient temperature). This was added dropwise to a solution of tetrakis(triphenylphosphine)palladium(O) (460 mg) and Ia (X=Ac, Y=H; 68.6 mg, 0.4 mmol) in tetrahydrofuran (0.95 ml) with stirring under argon. When no more reaction was evident by TLC (24 h), the solids were removed by filtration through a celite/silica/magnesium sulphate plug. The filtrate and washing were concentrated in vacuo and the residue chromatographed on silica (15:1 in dichloromethane:methanol) to give III (base=adenin-9-yl; Y=H) as a white solid, mp 188°–191° C. (21.8 mg, 22%) δH (CDCl$_3$) 1.75 (ddd, 1H, H-6'), 2.83 (ddd, 1H, H-6') 2.98–3.08 (M, 1H, H-4'), 3.58, 3.67 (each dd, 2H, CH$_2$OH), 5.66–5.73 (M, 1H, H-1'), 5.95 (ddd, 1H, H-2'), 6.22 (ddd, 1H, H-3'), 8.13 (S, 1H, H-2) and 8.20 (S, 1H, H-8), high resolution mass spectrum; Found (CI) 232-1198; calculated for M+H$^+$ (C$_{11}$H$_{13}$N$_5$O)=232-1198.

EXAMPLE 5

III (base=6-chloropurine, Y=Ph$_3$C)

By the method of Example 4, reaction of 6-chloropurine in DMF with sodium hydride, then with Ia (X=Ac, Y=Ph$_3$C) in the presence of Pd(PPh$_3$)$_4$ gave a 21% yield of III (base=6-chloropurinyl, Y=Ph$_3$C) as a white foam; high resolution mass spectrum; Found (CI) 493.1795; calculated for M+H$^+$ (C$_{30}$H$_{25}$N$_4$OCl)=493.1795.

EXAMPLE 6

III (base=6-chloropurine, Y=Ph$_3$C)

Diethyl azodicarboxylate (0.4 ml) was added dropwise to a solution of triphenylphosphine (670 mg, 2.6 mmol) and 6-chloropurine (391 mg) in tetrahydrofuran (THF) (8 ml) with stirring at room temperature under argon. After 5 min a solution of IIa (X=H, Y=Ph$_3$C; 323 mg, 0.91 mmol) in THF (1 ml) was added dropwise, and then the mixture was stirred overnight when TLC showed that reaction was complete. The solvent was removed in vacuo and the residual orange oil was chromatographed on silica (3:1 to 2:1 petrol:ethyl acetate) to give III as a white foam (212 mg, 47%) identical to that prepared by the method of Example 5.

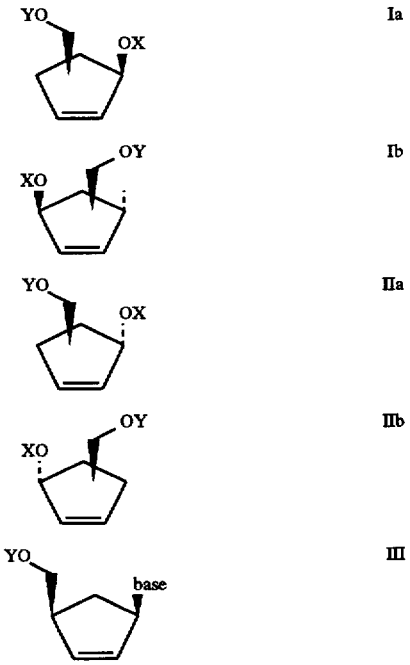

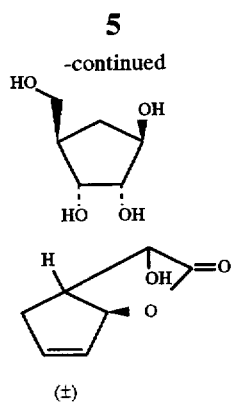

(±)

↓ 1

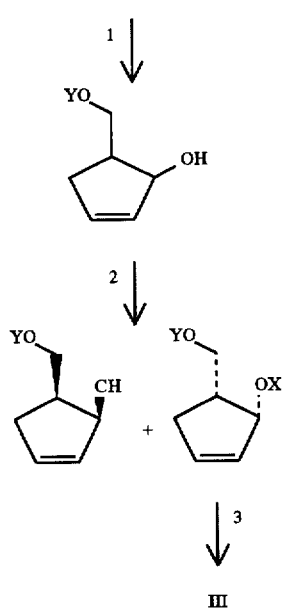

↓ 3

III

We claim:
1. An individual enantiomer, substantially free of its mirror image enantiomer, of a cyclopentene of the formula:

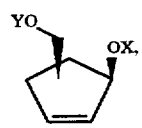 (Ia)

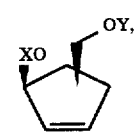 (Ib)

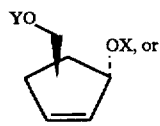 (IIa)

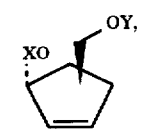 (IIb)

wherein OX at the 1-position is hydroxy or acyloxy;
wherein the CH₂OY group is at the 5-position, and OY is hydroxy or a protected hydroxy group, the protecting group being readily removed to produce a hydroxy group.

2. An individual enantiomer according to claim 1, wherein said protecting group, Y, is acyl, triarylmethyl or trialkylsilyl.

3. An individual enantiomer according to claim 1, wherein OX is acetoxy, and OY is OH.

4. An individual enantiomer according to claim 2, wherein OX is acetoxy.

5. A process for preparing an individual enantiomer, substantially free of its mirror image enantiomer, of a cyclopentene of the formula:

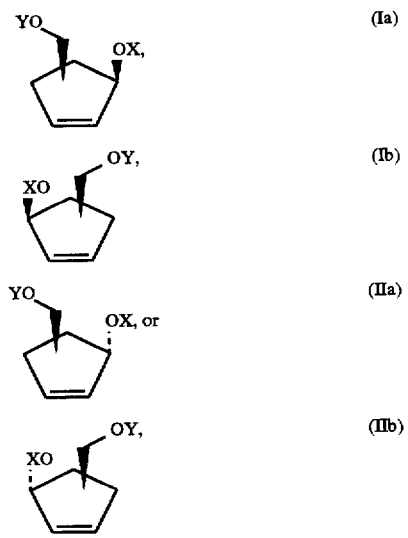

wherein OX at the 1-position is hydroxy or acyloxy;
wherein OY on the CH₂OY group which is at the 4 or 5-position is hydroxy or a protected hydroxy group, the protecting group being readily removed to produce a hydroxy group, comprising contacting a racemic mixture of protected secondary alcohols, Ia/Ib or IIa/IIb, wherein OX is OH and OY is protected hydroxy, and an acyl donor, with a lipase which selectively acylates one of the enantiomers in said racemic mixture, thereby producing a mixture of one unreacted enantiomer and the acyl ester of the other enantiomer; and separating the ester from the unreacted alcohol to produce said enantiomer.

6. A process according to claim 5, wherein said acyl donor is vinyl acetate or butyric anhydride.

7. A process according to claim 5, wherein said lipase is *Pseudomonas fluorescens* lipase.

8. A process according to claim 5, which further comprises reacting either: (i) the product ester, wherein OX is OAc; or (ii) a derivative of the product alcohol, wherein OX is a good leaving group; with a nucleoside-forming base, under displacement conditions, thereby forming an individual enantiomer of a nucleoside.

9. A process according to claim 8, wherein said ester, wherein OX is OAc, is reacted with a Pd(0) complex to form a π-allyl complex, which is then reacted with the basic salt of said nucleoside-forming base to form said nucleoside.

10. A process according to claim 8, wherein said derivative of the product alcohol, wherein OX is a good leaving group, is reacted with the basic salt of said nucleoside-forming base to form said nucleoside by direct $S^N2$ displacement.

11. A process according to claim 8, wherein said nucleoside-forming base is adenine or 6-chloropurine.

12. A process for preparing an individual enantiomer, substantially free of its mirror image enantiomer, of a cyclopentene of the formula:

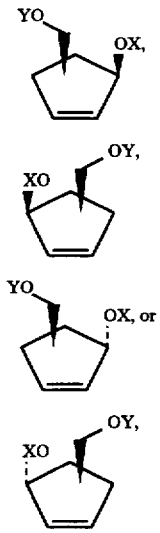

(Ia)

(Ib)

(IIa)

(IIb)

wherein OX at the 1-position is hydroxy or acyloxy; wherein OY on the CH$_2$OY group which is at the 4 or 5-position is hydroxy or a protected hydroxy group, the protecting group being readily removed to produce a hydroxy group, comprising contacting a racemic mixture of secondary alcohols, Ia/Ib or IIa/IIb, wherein OX is acyloxy, with a lipase which selectively deacylates one of the enantiomers in said racemic mixture, thereby producing a mixture of one unreacted acyloxy enantiomer and the corresponding secondary alcohol of the other enantiomer; and separating the unreacted ester from the alcohol to produce said enantiomer.

13. A process according to claim 12, wherein said lipase is *Pseudomonas fluorescens* lipase.

14. A process according to claim 12 which further comprises reacting the product ester, wherein OX is OAc, or a derivative of the product alcohol, wherein OX is a good leaving group, with a nucleoside-forming base, under displacement conditions, thereby forming an individual enantiomer of a nucleoside.

15. A process according to claim 14, wherein said ester, wherein OX is OAc, is reacted with a Pd(0) complex to form a π-allyl complex, which is then reacted with the basic salt of said nucleoside-forming base to form said nucleoside.

16. A process according to claim 14, wherein said derivative of the product alcohol, wherein OX is a good leaving group, is reacted with the basic salt of said nucleoside-forming base to form said nucleoside by direct $S^N2$ displacement.

17. A process according to claim 14, wherein said nucleoside-forming base is adenine or 6-chloropurine.

* * * * *